United States Patent
Samaritani et al.

(10) Patent No.: US 6,852,314 B1
(45) Date of Patent: Feb. 8, 2005

(54) IFN-β LIQUID FORMULATIONS

(75) Inventors: Fabrizio Samaritani, Rome (IT); Patrizia Natale, Rome (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 08/737,633

(22) PCT Filed: May 15, 1995

(86) PCT No.: PCT/EP95/01825

§ 371 (c)(1),
(2), (4) Date: Nov. 15, 1996

(87) PCT Pub. No.: WO95/31213

PCT Pub. Date: Nov. 23, 1995

(30) Foreign Application Priority Data

May 16, 1994 (IT) ........................................ RM94A0300

(51) Int. Cl.[7] .......................... A61K 38/21; C07K 1/00; C07K 14/00; C07K 17/00; B65D 47/02
(52) U.S. Cl. ........................ 424/85.6; 530/351; 514/12; 215/14; 215/49
(58) Field of Search ........................ 424/85.6; 530/351; 215/49, 14; 514/12

(56) References Cited

U.S. PATENT DOCUMENTS

| 4,465,622 A | | 8/1984 | Nobuhara et al. | ........... 260/112 |
|---|---|---|---|---|
| 4,647,454 A | * | 3/1987 | Cymbalista et al. | .......... 424/80 |
| 4,724,232 A | * | 2/1988 | Rideout et al. | ................ 514/50 |
| 5,004,605 A | * | 4/1991 | Hershenson et al. | ....... 424/85.6 |
| 5,183,746 A | | 2/1993 | Shaked et al. | ........... 435/69.51 |
| 5,643,566 A | * | 7/1997 | Hanisch et al. | ............ 424/85.4 |

FOREIGN PATENT DOCUMENTS

| EP | 89245 | 8/1983 |
|---|---|---|
| EP | 270799 | 6/1988 |
| WO | 8902750 | 4/1989 |
| WO | 89/04177 | 5/1989 |

OTHER PUBLICATIONS

Dialog Information Services, file 351, WPIL, Dialog accession no. 003925794, WPI accession no. 84–071338/12, Toray Ind Inc: "Stabilising beta–interferon having no sugar chain by adding polyol, e.g. ethylene glycol, glycerine or sugar, esp. oligo saccharide", JP 59025333, A, 840209, 8412 (Basic) Feb. 9, 1986.

* cited by examiner

Primary Examiner—Robert Landsman
(74) Attorney, Agent, or Firm—Dickstein, Shapiro, Morin & Oshinsky, LLP.

(57) ABSTRACT

Interferon-β liquid formulations stabilized with a polyol, a non-reducing sugar or an amino acid. In particular, the formulations are stabilized with a polyol, such as mannitol. The formulations, preferably, furthermore comprise a buffer, such as acetate buffer, at a pH comprised between 3.0 and 4.0 and human albumin at a minimum quantity. The interferon-β is preferably recombinant.

13 Claims, No Drawings

IFN-β LIQUID FORMULATIONS

This is a '371 of PCT/EP95/01825.

The present invention relates to liquid formulations of interferon-β (IFN-β) stabilised with a polyol, a non-reducing sugar or an amino acid. In particular, it relates to liquid formulations containing mannitol, human albumin and acetate buffer.

Interferons (alpha, β, gamma) are glycoproteins produced in the cells of vertebrates following induction. The most traditional inducers are virus, but also other microbial agents, other natural substances and synthetic compounds have the same behaviour.

Interferon-β is induced in human fibroblasts, has anti-viral activity, but in the therapy of some tumoral forms, other activities can be exploited together with the anti-viral activity, such as the anti-proliferative cellular activity and immunoregulatory activity.

Production from culture of human fibroblasts, and specifically from recombinant DNA techniques, now allows to obtain industrial quantities of interferon-β.

It is known that proteins in the purified form are especially susceptible to degradation, even due to the normal activity of atmospheric agents. This peculiarity becomes even more evident for proteins produced according to recombinant DNA techniques.

As a direct consequence of the fact that highly purified proteins are easily subject to denaturization, it becomes desirable to obtain stable formulations which ensure the longest possible life-cycle to the product.

Stabilisation of formulations containing highly purified proteins may be carried out by the addition of one or more excipients which inhibit or delay degradation of the active principle.

Pharmaceutical compositions containing interferon-β are well known. EP Patent application 89 245 (INTER-YEDA Ltd) describes a lyophilised composition of interferon-β containing mannitol, human albumin and polyvinylpyrrolidone, the latter as stabilising agent. Also known are pharmaceutical liquid compositions containing other interferons.

International Patent Application WO 89/04177 (GENENTECH—Priority Mar. 11, 1987) describes liquid pharmaceutical formulations of gamma-interferon comprising a buffer which maintains the pH within the range of 4.0–6.0, a polyhydroxylate sugar as stabiliser and a non-ionic detergent.

EP Patent Application 270 799 describes IFN-β pharmaceutical compositions in liquid form or lyophilized, which comprise, as solubilizer/stabilizer, one or more non-ionic polymeric detergents.

It is highly desirable to obtain such liquid formulations in order to avoid the reconstitution of lyophilised preparations and thus to permit ease of use.

It has now surprisingly been found that liquid pharmaceutical formulations comprising interferon-β stabilised with a polyol, a non-reducing sugar or an amino acid in an appropriate buffer result particularly stable and maintain biological activity for a long period of time.

The main object of the present invention is to provide a liquid pharmaceutical formulation comprising interferon-β and a polyol, a non-reducing sugar or an amino acid, as stabiliser.

Preferably the stabiliser is selected from mannitol, saccharose and glycine: more preferably, the stabiliser is mannitol.

Preferably the liquid pharmaceutical formulation comprises a buffer with a pH between 3 and 4; more preferably, acetate buffer.

Another object of this invention is to provide a process for the preparation of such liquid pharmaceutical formulation comprising the stage of dilution of IFN-β with a solution of the excipients.

Yet another object of the present invention is to provide a presentation form of the liquid pharmaceutical formulation comprising the previously mentioned formulation, hermetically sealed under sterile conditions in a container suitable for storage prior to use.

To study the stability of liquid formulations of IFN-β, various formulations were prepared diluting bulk IFN-β in different buffers at varying pH, then storing the samples at different temperatures and carrying out assays with the immunological test at set intervals of time. Once the buffer solution and the preferred pH, with which the greater stability is obtained, have been selected, then the stabilised formulations of the invention are prepared by diluting the interferon bulk solution with the buffer solution containing also the excipients. Stability of the various formulations was determined by measuring the residual activity of IFN-β at fixed intervals of time, after storage of the solution at the temperatures of 50° C., 37° C. and 25° C.

To determine such activity, samples were assayed under immunological and biological tests.

The immunological test was carried out by using the TORAY kit (Human IFN-β ELISA Kit, TORAY INDUSTRIES, Inc.), following the methodology reported in the enclosed instructions.

The biological dosage was performed as described by Armstrong J. A (1981). Cytopathic effect inhibition assay for Interferon, in Methods in Enzymology 73 381–387. This test permits the measuring of WEN-D activity by exploiting its ant-viral capacity.

Measure of activity is expressed in International Units per milliliter of solution (IU/ml) or in Mega International Units per milliliter of solution (MIU/ml). (1 MIU/ml=1,000,000 IU/ml).

An International Unit is calculated as described in the Research Reference Reagent Note No. 35, published by the National Institute of Health, Bethesda. Md., in relation to the HuIFN-β NIH Reference Reagent Gb 23-902-531 used as standard.

The measurement is reported here as percentage of residual activity of the sample of Interferon-β in the various formulations, taking activity of the sample at time zero as equal to 100%.

Dosages were carried out in duplicate.

To assess the effect of the pH on stability of the active ingredient, different formulations of recombinant IFN-β were prepared containing 0.6 and 1 MIU/ml with various buffer solutions, i.e. acetate buffer, citrate buffer, ascorbate buffer, succinate buffer.

The formulations containing recombinant IFN-β with the buffer solutions were prepared and stored at temperatures of 50° C., 37° C. and 25° C. then assayed under the immunological test at set time intervals. The formulations were prepared in such a way as to have a pH between 3.0 and 4.0 and between 5.0 and 6.0, all with buffer at a concentration of 0.01 M.

Tables 1, 2 and 3 report results of tests carried out at set intervals of time, from 1 to 42 days, at the various temperatures.

Data contained in the above-mentioned tables indicate that the formulations with a pH between 5.0 and 6.0 show an immediate loss of titre. Formulations with pH between 3.0 and 4.0 show, however, a high stability, especially in the presence of acetate buffer.

To assess the effect of excipients on the stability of the active principle, different formulations were prepared containing 1 MIU/ml of recombinant IFN-β, using various excipients such as mannitol, saccharose or an amino acid such as glycine, and human albumin already partially contained in the interferon-β bulk solution.

Quantities of mannitol, saccharose or glycine used were such as to obtain isotonic solutions of IFN-β.

Stability studies on these formulations were carried out by maintaining samples at 50° C., 37° C., 25° C. and 4° C., and measuring residual activity at the times reported in tables 4 and 5.

Data reported in tables 4 and 5 show that degradation in the formulations containing a polyol like mannitol is much lower in respect to those formulations containing saccharose or glycine.

The formulation selected for a deeper study was the one containing mannitol in 0.01 M acetate buffer at pH 3.5, which was subjected to further tests: for evaluatation of the effect on stability of the ionic force and the albumin.

Solutions of IFN-β in 0.01 M acetate buffer at pH 3.5, were prepared at different values of osmolality: 150, 300 and 400, and with different dielectric constants, with 5, 10, and 20% propylene glycol, and samples were then stored and assayed at 50° C., 37° C. and 25° C. The study shows that increase of osmolality and the propylene glycol content decreased stability of the liquid formulations of IFN-β.

Since bulk IFN-β contains albumin, it was decided to proceed to a study for evaluation of the effect of albumin on the stability of interferon-β liquid formulations. Samples containing IFN-β (1 MIU/ml) and the acetate buffer solution at pH 3.5 were added to 1, 3, 6, and 9 mg/ml of human albumin and tested at temperatures of 50° C., 37° C. and 25° C.

Results show that with the increase of albumin the stability of the samples decreased. The albumin content per sample was fixed in such a way as to have the minimum quantity compatible with that contained in the various bulks: in a formulation containing 1 MIU/ml of IFN-β, a uniform content of 0.5 mg/ml albumin is maintained.

Examples of Pharmaceutical Production

Materials: mannitol (Merck); human albumin (Boehring); 0.01 M acetate buffer (Merck); NaOH 1 M (Merck).

DIN 2R glass bottles (glass type I borosilicate glass) with stoppers of Pharmagummi rubber, butylic mixture, and aluminium ring, were used a containers.

Example of Preparation of r-IFN-β Solution

A) Solution at 1 MIU/ml

For the preparation of a batch of 1 Lt. of finished product, the following quantities are used:

| | |
|---|---|
| r-interferon-beta | 1000 MIU |
| Mannitol | 54.6 g |
| Human albumin | 0.5 g-P |
| 0.01 M pH 3.5 acetate buffer | q.s. to 1 Lt. |

P = amount of human albumin present in bulk interferon.

B) Solution at 12 MIU/ml

For the preparation of a batch of 1 Lt. of finished product, the following quantities are used:

| | |
|---|---|
| r-interferon-beta | 12000 MIU |
| Mannitol | 54.6 g |
| Human albumin | 4.0 g-P |
| 0.01 M pH 3.5 acetate buffer | q.s. to 1 Lt. |

P = amount of human albumin present in bulk interferon.

C) Solution at 24 MIU/ml

For the preparation of a batch of 1 Lt. of finished product, the following quantities are used:

| | |
|---|---|
| r-interferon-beta | 24000 MIU |
| Mannitol | 54.6 g |
| Human albumin | 8.0 g-P |
| 0.01 M pH 3.5 acetate buffer | q.s. to 1 Lt. |

P = amount of human albumin present in bulk interferon.

Method of Preparation

The required quantity of mannitol and human albumin (taking into account the quantity of albumin present in the bulk) is dissolved in approximately 500 g of 0.01 M pH 3.5 acetate buffer. The pH is checked and, if necessary, adjusted to the value of 3.5±0.2 with diluted (1:2) acetic acid or with 1 M NaOH.

The solution is brought to the final weight of 1 Kg with 0.01 M pH 3.5 acetate buffer.

The required quantity of r-interferon β is weighed in a beaker and brought to the final weight of 500 g with the solution of excipients.

In another beaker, 500 g of solution of excipients is weighed. The 500 g of solution containing interferon-β is filtered on a sterile membrane of 0.22 μm (DURAPORE) at a pressure not exceeding 1.5 atm. The sterile solution is collected in a glass erlenmeyer flask. Immediately afterwards the 500 g of excipient solution is filtered on the same membrane at a pressure of 1.5 atm and collected in the same erlenmeyer flask. The solution obtained is slowly mixed.

TABLE 1 r-INTERFERON-β
LIQUID FORMULATION: 1 MIU/BOTTLE
RESULTS IMMUNOLOGICAL DOSAGE:
CONCENTRATION (%)
STABILITY IN 0.01 M CITRATE BUFFER AT DIFFERENT pH VALUES

| | | 50° C. | | 37° C. | | 25° C. | |
|---|---|---|---|---|---|---|---|
| | T = 0 | 1 D | 30 D | 19 D | 30 D | 12 D | 19 D |
| IFN/3 | 100 | 73.0 | 8.6 | 88.5 | 69.9 | 100 | 97.5 |
| (890600 IU/ML) | | | | | | | |
| IFN/4 | 100 | 20.1 | 1.0 | 68.7 | 36.6 | 100 | 62.8 |
| (820900 IU/ML) | | | | | | | |
| IFN/5 | 100 | ND | | | | | 43.6 |
| (532100 IU/ML) | | | | | | | |
| IFN/6 | 100 | ND | | | | | |
| (179500 IU/ML) | | | | | | | |

D = day(s)
ND = non-determinable
IFN/3 = formulation in citrate buffer pH 3.0
IFN/4 = formulation in citrate buffer pH 4.0
IFN/5 = formulation in citrate buffer pH 5.0
IFN/6 = formulation in citrate buffer pH 6.0

TABLE 2 r-INTERFERON-β
LIQUID FORMULATION: 0.6 MIU/BOTTLE
RESULTS IMMUNOLOGICAL DOSAGE:
CONCENTRATION (%)
STABILITY IN 0.01 M ACETATE BUFFER AT DIFFERENT pH VALUES

| | | 50° C. | | 37° C. | | 25° C. | |
|---|---|---|---|---|---|---|---|
| | T = 0 | 1 D | 30 D | 19 D | 30 D | 7 D | 19 D |
| IFN/3 | 100 | 72.6 | 48.3 | 97.5 | 100 | 100 | 100 |
| (549425 IU/ML) | | | | | | | |
| IFN/4 | 100 | 77.6 | 30.3 | 91.9 | 92.2 | | 100 |
| (459600 IU/ML) | | | | | | | |
| IFN/5 | 100 | 45.0 | | | | | |
| (52275 IU/ML) | | | | | | | |
| IFN/6 | 100 | 57.2 | | | | | |
| (25425 IU/ML) | | | | | | | |

D = day(s)
IFN/3 = formulation in acetate buffer pH 3.0
IFN/4 = formulation in acetate buffer pH 4.0
IFN/5 = formulation in acetate buffer pH 5.0
IFN/6 = formulation in acetate buffer pH 6.0

TABLE 3 r-INTERFERON-β
LIQUID FORMULATION: 1 MIU/BOTTLE
RESULTS IMMUNOLOGICAL DOSAGE: CONCENTRATION (%)
STABILITY IN 0.01 M ASCORBATE & SUCCINATE BUFFER AT pH 3.00 & 4.00

|  |  | 50° C. | | | 37° C. | | 25° C. | | |
| --- | --- | --- | --- | --- | --- | --- | --- | --- | --- |
|  | T = 0 | 7 D | 14 D | 21 D | 7 D | 42 D | 7 D | 14 D | 42 D |
| IFN/3/ASC | 100 (1068400 IU/ML) | ND | | | 32.4 | | 76.5 | 10.5 | |
| IFN/4/ASC | 100 (1025000 IU/ML) | ND | | | 15.6 | | 80.6 | | |
| IFN/3/SUC | 100 (980200 IU/ML) | 62.9 | 54.8 | 22.1 | 92.7 | 87.8 | 96.0 | 62.5 | 97.2 |
| IFN/4/SUC | 100 (957600 IU/ML) | 62.8 | 43.8 | 22.7 | 88.5 | 14.3 | | 78.7 | 84.7 |

D = days
ND = non-determinable
IFN/3/ASC = formulation in ascorbic buffer pH 3.0;
IFN/4/ASC = formulation in ascorbic buffer pH 4.0;
IFN/3/SUC = formulation in succinate buffer pH 3.0;
IFN/4/SUC = formulation in succinate buffer pH 4.0

TABLE 4 r-INTERFERON-β
LIQUID FORMULATION: 1 MIU/BOTTLE
RESULTS BIOLOGICAL DOSAGE: CONCENTRATION (%)
STABILITY IN 0.01 M ACETATE BUFFER AT pH 3.5 with DIFFERENT EXCIPIENTS

|  |  | 50° C. | 37° C. | | 25° C. | | |
| --- | --- | --- | --- | --- | --- | --- | --- |
|  | T = 0 | 49 D | 49 D | 3 M | 3 M | 6 M | 9 M |
| ACE/SAC/3.5 | 100 (970000 IU/ML) | 25.8 | 100 | 85.6 | 100 | 100 | |
| ACE/MAN/3.5 | 100 (1150000 IU/ML) | 67.8 | 100 | 90.4 | 91.3 | 100 | 85.2 |
| ACE/GLY/3.5 | 100 (1200000 IU/ML) | 49.2 | 100 | 75.8 | 90.0 | 98.3 | |

D = days
M = months
ACE/SAC/3.5 = formulation in acetate buffer pH 3.5 + saccharose
ACE/MAN/3.5 = formulation in acetate buffer pH 3.5 + mannitol
ACE/GLY/3.5 = formulation in acetate buffer pH 3.5 + glycine

TABLE 5 r-INTERFERON-β
LIQUID FORMULATION: 1 MIU/BOTTLE
RESULTS IMMUNOLOGICAL DOSAGE: CONCENTRATION (%)
STABILITY USING DIFFERENT EXCIPIENTS IN 0.01 M ACETATE BUFFER AT pH 3.5

|  |  | 50° C. | | | 37° C. | | 25° C. | | | 4° C. | | |
| --- | --- | --- | --- | --- | --- | --- | --- | --- | --- | --- | --- | --- |
|  | T = 0 | 7 D | 14 D | 49 D | 14 D | 49 D | 3 M | 6 M | 9 M | 3 M | 6 M | 9 M |
| ACE/SAC/3.5 | 100 (1120000 IU/ML) | 78.6 | 62.5 | 10.3 | 99.1 | 96.4 | 67.1 | 97.2 | | 100 | 100 | |
| ACE/MAN/3.5 | 100 (1070000 IU/ML) | 90.6 | 74.8 | 60.3 | 100 | 100 | 100 | 100 | 100 | | 100 | 100 |
| ACE/GLY/3.5 | 100 (1220000 IU/ML) | 77.0 | 47.5 | 19.4 | 100 | 91.0 | 93.9 | 96.9 | | 87.7 | 100 | |

D = days
M = months
ACE/SAC/3.5 = formulation in acetate buffer pH 3.5 + saccharose
ACE/MAN/3.5 = formulation in acetate buffer pH 3.5 + mannitol
ACE/GLY/3.5 = formulation in acetate buffer pH 3.5 + glycine

What is claimed is:

1. A liquid pharmaceutical formulation consisting of from about 0.6 to 24 MIU/ml of interferon-β, mannitol, an acetate buffer at a pH between 3.0 and 4.0 and, optionally, albumin.

2. A liquid pharmaceutical formulation according to claim 1, in which interferon-β is recombinant.

3. A liquid pharmaceutical formulation according to claim 1, in which interferon-β is in a quantity between 0.6 and 1 MIU/ml.

4. A liquid pharmaceutical formulation according to claim 3, in which the buffer solution has a concentration of 0.01 M.

5. A liquid pharmaceutical formulation according to claim 1, in which the optional albumin is present and comprises human albumin.

6. A liquid pharmaceutical formulation according to claim 1, comprising 1 MIU/ml of interferon-β, 54.6 mg/ml of mannitol, 0.5 mg/ml of albumin in a solution of 0.01 M acetate buffer at pH 3.5.

7. A process for the preparation of a liquid pharmaceutical formulation according to claim 1, comprising combining interferon-β with mannitol, an acetate buffer at a pH between 3.0 and 4.0 and, optionally, albumin.

8. A container hermetically sealed in sterile conditions comprising the liquid pharmaceutical formulation according to claim 1 and appropriate for storage prior to use.

9. A process for the preparation of a liquid pharmaceutical formulation according to claim 7 in which interferon-β is recombinant and is in a quantity between 0.6 and 1 MIU/ml.

10. A process for the preparation of a liquid pharmaceutical formulation according to claim 9 in which conditions comprising interferon-β at 1 MIU/ml, mannitol at 54.6 mg/ml, and 0.5 mg/ml of albumin in a solution of 0.01 M acetate buffer at pH 3.5 are employed.

11. A container hermetically sealed in sterile conditions comprising the liquid pharmaceutical formulation according to claim 6 and appropriate for storage prior to use.

12. A container hermetically sealed in sterile conditions comprising the liquid pharmaceutical formulation according to claim 2 and appropriate for storage prior to use.

13. A liquid pharmaceutical formulation according to claim 6, in which interferon-β is recombinant.

* * * * *